(12) United States Patent
Dorn et al.

(10) Patent No.: US 9,078,779 B2
(45) Date of Patent: Jul. 14, 2015

(54) HAND-HELD ACTUATOR DEVICE

(75) Inventors: Jürgen Dorn, Neulussheim, DE (US);
Martin Wübbeling, Mannheim (DE);
Michael Vogel, Karlsruhe (DE)

(73) Assignee: C. R. Bard, Inc., Murray Hill, NJ (US)

( * ) Notice: Subject to any disclaimer, the term of this patent is extended or adjusted under 35 U.S.C. 154(b) by 1878 days.

(21) Appl. No.: 12/376,670

(22) PCT Filed: Aug. 7, 2007

(86) PCT No.: PCT/EP2007/058205
§ 371 (c)(1),
(2), (4) Date: Feb. 6, 2009

(87) PCT Pub. No.: WO2008/017683
PCT Pub. Date: Feb. 14, 2008

(65) Prior Publication Data
US 2010/0168756 A1    Jul. 1, 2010

(30) Foreign Application Priority Data

Aug. 7, 2006  (GB) .................................. 0615658.2

(51) Int. Cl.
| | | |
|---|---|---|
| *A61F 11/00* | (2006.01) | |
| *A61F 2/95* | (2013.01) | |
| *A61F 2/966* | (2013.01) | |
| *A61M 25/01* | (2006.01) | |

(52) U.S. Cl.
CPC . *A61F 2/95* (2013.01); *A61F 2/966* (2013.01); *A61F 2002/9517* (2013.01); *A61M 25/0147* (2013.01); *A61M 2025/015* (2013.01)

(58) Field of Classification Search
CPC .... A61F 2002/9517; A61F 2/95; A61F 2/966
USPC .............................. 606/108; 623/1.11; 74/575
See application file for complete search history.

(56) References Cited

U.S. PATENT DOCUMENTS

| | | | |
|---|---|---|---|
| 1,988,060 | A | 1/1935 | Vollenbroich |
| 2,831,356 | A * | 4/1958 | Wiman .......................... 74/128 |
| 2,934,211 | A | 4/1960 | Shivek |
| 2,939,680 | A | 6/1960 | Powell |
| 3,070,057 | A | 12/1962 | Dezzani |

(Continued)

FOREIGN PATENT DOCUMENTS

| | | |
|---|---|---|
| CA | 2155527 A1 | 8/1994 |
| DE | 02544371 A1 | 4/1976 |

(Continued)

OTHER PUBLICATIONS

Bridge SE Binary System, Oct. 2002, 3 pages, http:/www.medtronicave/com/includes/content/phsycians/bridges/htm.

(Continued)

*Primary Examiner* — Victor Nguyen
*Assistant Examiner* — Kevin Everage
(74) *Attorney, Agent, or Firm* — Buchalter Nemer

(57) ABSTRACT

A hand-held actuator device for releasing into the body from a delivery system a medical prosthesis, like a stent, comprising a frame (10) that acts as a housing, a reel (30) for receiving a wire (8), a manually operable slider (34) mounted to the frame and a one-way connection between the slider and the reel. Actuating the slider causes the reel to wind up the wire and release the medical prosthesis.

20 Claims, 3 Drawing Sheets

(56) References Cited

U.S. PATENT DOCUMENTS

| | | | |
|---|---|---|---|
| 3,137,176 A * | 6/1964 | Wright | 74/142 |
| 3,562,427 A | 2/1971 | Yano et al. | |
| 3,585,707 A | 6/1971 | Stevens | |
| 3,871,382 A | 3/1975 | Mann | |
| 3,881,423 A | 5/1975 | Woods et al. | |
| 4,256,113 A | 3/1981 | Chamness | |
| 4,553,545 A | 11/1985 | Maass et al. | |
| 4,580,568 A | 4/1986 | Gianturco | |
| 4,616,648 A | 10/1986 | Simpson | |
| 4,649,922 A | 3/1987 | Wiktor | |
| 4,665,918 A | 5/1987 | Garza et al. | |
| 4,723,547 A | 2/1988 | Kullas et al. | |
| 4,733,665 A | 3/1988 | Palmaz | |
| 4,739,762 A | 4/1988 | Palmaz | |
| 4,760,622 A | 8/1988 | Rohrman | |
| 4,771,773 A | 9/1988 | Kropf | |
| 4,800,882 A | 1/1989 | Gianturco | |
| 4,856,516 A | 8/1989 | Hillstead | |
| 4,886,062 A | 12/1989 | Wiktor | |
| 4,889,112 A | 12/1989 | Schachner et al. | |
| 4,913,141 A | 4/1990 | Hillstead | |
| 4,913,683 A | 4/1990 | Gregory | |
| 4,969,458 A | 11/1990 | Wiktor | |
| 4,990,151 A | 2/1991 | Wallsten | |
| 5,019,090 A | 5/1991 | Pinchuk | |
| 5,026,377 A | 6/1991 | Burton et al. | |
| 5,045,072 A | 9/1991 | Castillo et al. | |
| 5,049,128 A | 9/1991 | Duquette | |
| 5,054,162 A | 10/1991 | Rogers | |
| 5,102,417 A | 4/1992 | Palmaz | |
| 5,104,404 A | 4/1992 | Wolff | |
| 5,116,365 A | 5/1992 | Hillstead | |
| 5,133,732 A | 7/1992 | Wiktor | |
| 5,135,536 A | 8/1992 | Hillstead | |
| 5,161,547 A | 11/1992 | Tower | |
| 5,163,941 A | 11/1992 | Garth et al. | |
| 5,190,552 A | 3/1993 | Kelman | |
| 5,201,757 A | 4/1993 | Heyn et al. | |
| 5,203,774 A | 4/1993 | Gilson et al. | |
| 5,209,754 A | 5/1993 | Ahluwalia | |
| 5,224,939 A | 7/1993 | Holman et al. | |
| 5,228,452 A | 7/1993 | Samson | |
| 5,242,423 A | 9/1993 | Goodsir et al. | |
| 5,254,107 A | 10/1993 | Soltesz | |
| 5,275,622 A | 1/1994 | Lazarus et al. | |
| 5,279,596 A | 1/1994 | Castaneda et al. | |
| 5,282,824 A | 2/1994 | Gianturco | |
| 5,290,295 A | 3/1994 | Querals et al. | |
| 5,290,310 A | 3/1994 | Makower et al. | |
| 5,292,331 A | 3/1994 | Boneau | |
| 5,312,351 A | 5/1994 | Gerrone | |
| 5,312,363 A | 5/1994 | Ryan et al. | |
| 5,334,147 A | 8/1994 | Johnson | |
| 5,336,192 A | 8/1994 | Palestrant | |
| 5,346,498 A | 9/1994 | Greelis et al. | |
| 5,380,283 A | 1/1995 | Johnson | |
| 5,383,892 A | 1/1995 | Cardon et al. | |
| 5,387,235 A | 2/1995 | Chuter | |
| 5,391,172 A | 2/1995 | Williams et al. | |
| 5,411,507 A | 5/1995 | Heckele | |
| 5,415,664 A | 5/1995 | Pinchuk | |
| 5,417,708 A | 5/1995 | Hall et al. | |
| 5,421,955 A | 6/1995 | Lau et al. | |
| 5,433,723 A | 7/1995 | Lindenberg et al. | |
| 5,443,477 A | 8/1995 | Marin et al. | |
| 5,449,373 A | 9/1995 | Pinchasik et al. | |
| 5,456,694 A | 10/1995 | Marin et al. | |
| 5,456,713 A | 10/1995 | Chuter | |
| 5,458,615 A | 10/1995 | Klemm et al. | |
| 5,466,221 A | 11/1995 | Zadini et al. | |
| 5,480,423 A | 1/1996 | Ravenscroft et al. | |
| 5,507,768 A | 4/1996 | Lau et al. | |
| 5,507,769 A | 4/1996 | Marin et al. | |
| 5,509,900 A | 4/1996 | Kirkman | |
| 5,514,154 A | 5/1996 | Lau et al. | |
| 5,531,690 A | 7/1996 | Solar | |
| 5,536,248 A | 7/1996 | Weaver et al. | |
| 5,538,510 A | 7/1996 | Fontirroche et al. | |
| 5,556,389 A | 9/1996 | Liprie | |
| 5,562,726 A | 10/1996 | Chuter | |
| 5,562,728 A | 10/1996 | Lazarus et al. | |
| 5,569,296 A | 10/1996 | Marin et al. | |
| 5,571,086 A | 11/1996 | Kaplan et al. | |
| 5,571,172 A | 11/1996 | Chin | |
| 5,573,530 A | 11/1996 | Fleury et al. | |
| 5,578,074 A | 11/1996 | Mirigian | |
| 5,591,172 A | 1/1997 | Bachmann et al. | |
| 5,591,196 A | 1/1997 | Marin et al. | |
| 5,601,568 A | 2/1997 | Chevillon et al. | |
| 5,603,721 A | 2/1997 | Lau et al. | |
| 5,603,801 A | 2/1997 | DeFriese et al. | |
| 5,605,530 A | 2/1997 | Fischell et al. | |
| 5,609,627 A | 3/1997 | Goicoechea et al. | |
| 5,618,300 A | 4/1997 | Marin et al. | |
| 5,628,755 A | 5/1997 | Heller et al. | |
| 5,630,801 A | 5/1997 | Roussigne et al. | |
| 5,645,076 A | 7/1997 | Yoon | |
| 5,649,906 A | 7/1997 | Gory et al. | |
| 5,666,970 A | 9/1997 | Smith | |
| 5,669,936 A | 9/1997 | Lazarus | |
| 5,672,179 A | 9/1997 | Garth et al. | |
| 5,674,278 A | 10/1997 | Boneau | |
| 5,681,322 A | 10/1997 | Hartigan, Jr. | |
| 5,683,345 A | 11/1997 | Waksman et al. | |
| 5,683,451 A | 11/1997 | Lenker et al. | |
| 5,690,644 A | 11/1997 | Yurek et al. | |
| 5,693,084 A | 12/1997 | Chuter | |
| 5,695,498 A | 12/1997 | Tower | |
| 5,695,499 A | 12/1997 | Helgerson et al. | |
| 5,695,517 A | 12/1997 | Marin et al. | |
| 5,697,936 A | 12/1997 | Shipko et al. | |
| 5,697,949 A | 12/1997 | Giurtino et al. | |
| 5,704,914 A | 1/1998 | Stocking et al. | |
| 5,707,376 A | 1/1998 | Kavteladze et al. | |
| 5,709,703 A | 1/1998 | Lukic et al. | |
| 5,713,917 A | 2/1998 | Leonhardt et al. | |
| 5,713,948 A | 2/1998 | Uflacker | |
| 5,716,365 A | 2/1998 | Goicoechea et al. | |
| 5,716,393 A | 2/1998 | Lindenberg et al. | |
| 5,720,776 A | 2/1998 | Chuter et al. | |
| 5,725,534 A | 3/1998 | Rasmussen | |
| 5,728,158 A | 3/1998 | Lau et al. | |
| 5,733,303 A | 3/1998 | Israel et al. | |
| 5,735,893 A | 4/1998 | Lau et al. | |
| 5,738,667 A | 4/1998 | Solar | |
| 5,741,298 A | 4/1998 | MacLeod | |
| 5,749,921 A | 5/1998 | Lenker et al. | |
| 5,755,777 A | 5/1998 | Chuter | |
| 5,759,186 A | 6/1998 | Bachmann et al. | |
| 5,766,184 A | 6/1998 | Matsuno et al. | |
| 5,769,871 A | 6/1998 | Mers Kelly et al. | |
| 5,776,141 A | 7/1998 | Klein et al. | |
| 5,776,142 A | 7/1998 | Gunderson | |
| 5,776,161 A | 7/1998 | Globerman et al. | |
| 5,776,186 A | 7/1998 | Uflacker | |
| 5,780,807 A | 7/1998 | Saunders | |
| 5,782,855 A | 7/1998 | Lau et al. | |
| 5,788,707 A | 8/1998 | Del Toro et al. | |
| 5,795,325 A | 8/1998 | Valley et al. | |
| 5,800,456 A | 9/1998 | Maeda et al. | |
| 5,800,520 A | 9/1998 | Fogarty et al. | |
| 5,807,327 A | 9/1998 | Green et al. | |
| 5,810,768 A | 9/1998 | Lopez | |
| 5,810,837 A | 9/1998 | Hofmann et al. | |
| 5,810,869 A | 9/1998 | Kaplan et al. | |
| 5,810,872 A | 9/1998 | Kanesaka et al. | |
| 5,814,062 A | 9/1998 | Sepetka et al. | |
| 5,824,058 A | 10/1998 | Ravenscroft et al. | |
| 5,833,694 A | 11/1998 | Poncet | |
| 5,840,064 A | 11/1998 | Liprie | |
| 5,843,088 A | 12/1998 | Barra et al. | |
| 5,843,092 A | 12/1998 | Heller et al. | |
| 5,843,120 A | 12/1998 | Israel et al. | |
| 5,843,244 A | 12/1998 | Pelton et al. | |

(56) References Cited

U.S. PATENT DOCUMENTS

| | | | |
|---|---|---|---|
| 5,851,210 | A | 12/1998 | Torossian |
| 5,860,998 | A | 1/1999 | Robinson et al. |
| RE36,104 | E | 2/1999 | Solar |
| 5,868,755 | A | 2/1999 | Kanner et al. |
| 5,873,906 | A | 2/1999 | Lau et al. |
| 5,879,382 | A | 3/1999 | Boneau |
| 5,891,154 | A | 4/1999 | Loeffler |
| 5,906,579 | A | 5/1999 | Vander Salm et al. |
| 5,906,619 | A | 5/1999 | Olson et al. |
| 5,913,897 | A | 6/1999 | Corso, Jr. et al. |
| 5,919,225 | A | 7/1999 | Lau et al. |
| 5,925,061 | A | 7/1999 | Ogi et al. |
| 5,928,246 | A | 7/1999 | Gordon et al. |
| 5,931,842 | A | 8/1999 | Goldsteen et al. |
| 5,944,727 | A | 8/1999 | Ahari et al. |
| 5,951,585 | A | 9/1999 | Cathcart et al. |
| 5,961,536 | A | 10/1999 | Mickley et al. |
| 5,968,052 | A | 10/1999 | Sullivan, III et al. |
| 5,968,053 | A | 10/1999 | Revelas |
| 5,968,068 | A | 10/1999 | Dehdashtian et al. |
| 5,968,069 | A | 10/1999 | Dusbabek et al. |
| 5,972,018 | A | 10/1999 | Israel et al. |
| 5,980,515 | A | 11/1999 | Tu |
| 5,984,225 | A | 11/1999 | Enzinna |
| 5,992,000 | A | 11/1999 | Humphrey et al. |
| 5,997,562 | A | 12/1999 | Zadno-Azizi et al. |
| 6,004,328 | A | 12/1999 | Solar |
| 6,015,429 | A | 1/2000 | Lau et al. |
| 6,019,778 | A | 2/2000 | Wilson et al. |
| 6,027,509 | A | 2/2000 | Schatz et al. |
| 6,039,744 | A | 3/2000 | Forber |
| 6,039,749 | A | 3/2000 | Marin et al. |
| 6,042,597 | A | 3/2000 | Kveen et al. |
| 6,045,536 | A | 4/2000 | Meier et al. |
| 6,071,263 | A | 6/2000 | Kirkman |
| 6,071,286 | A | 6/2000 | Mawad |
| 6,077,295 | A | 6/2000 | Limon et al. |
| 6,080,140 | A | 6/2000 | Swaminathan et al. |
| 6,083,194 | A | 7/2000 | Lopez |
| 6,090,035 | A | 7/2000 | Campbell et al. |
| 6,090,063 | A | 7/2000 | Makower et al. |
| 6,090,128 | A | 7/2000 | Douglas |
| 6,096,009 | A | 8/2000 | Windheuser et al. |
| 6,096,045 | A | 8/2000 | Del Toro et al. |
| 6,096,056 | A | 8/2000 | Brown |
| 6,102,942 | A | 8/2000 | Ahari |
| 6,110,191 | A | 8/2000 | Dehdashtian et al. |
| 6,113,607 | A | 9/2000 | Lau et al. |
| 6,117,140 | A | 9/2000 | Munsinger |
| 6,117,165 | A | 9/2000 | Becker |
| 6,117,167 | A | 9/2000 | Goicoechea et al. |
| 6,123,723 | A | 9/2000 | Konya et al. |
| 6,129,755 | A | 10/2000 | Mathis et al. |
| 6,136,007 | A | 10/2000 | Goldsteen et al. |
| 6,136,572 | A | 10/2000 | Benatti et al. |
| 6,143,014 | A | 11/2000 | Dehdashtian et al. |
| 6,143,021 | A | 11/2000 | Staehle |
| 6,146,415 | A | 11/2000 | Fitz |
| 6,149,680 | A | 11/2000 | Shelso et al. |
| 6,156,053 | A | 12/2000 | Gandhi et al. |
| 6,156,054 | A | 12/2000 | Zadno-Azizi et al. |
| 6,156,063 | A | 12/2000 | Douglas |
| 6,159,228 | A | 12/2000 | Frid et al. |
| 6,159,239 | A | 12/2000 | Greenhalgh |
| 6,167,315 | A | 12/2000 | Coe et al. |
| 6,168,610 | B1 | 1/2001 | Marin et al. |
| 6,168,617 | B1 | 1/2001 | Blaeser et al. |
| 6,174,327 | B1 | 1/2001 | Mertens et al. |
| 6,183,509 | B1 | 2/2001 | Dibie |
| 6,190,360 | B1 | 2/2001 | Iancea et al. |
| 6,190,393 | B1 | 2/2001 | Bevier et al. |
| 6,190,406 | B1 | 2/2001 | Duerig et al. |
| 6,203,550 | B1 | 3/2001 | Olson |
| 6,203,558 | B1 | 3/2001 | Dusbabek et al. |
| 6,210,422 | B1 | 4/2001 | Douglas |
| 6,217,585 | B1 | 4/2001 | Houser et al. |
| 6,224,608 | B1 | 5/2001 | Ciccolella et al. |
| 6,238,402 | B1 | 5/2001 | Sullivan, III et al. |
| 6,238,415 | B1 | 5/2001 | Sepetka et al. |
| 6,241,692 | B1 | 6/2001 | Tu et al. |
| 6,245,100 | B1 | 6/2001 | Davila et al. |
| 6,248,122 | B1 | 6/2001 | Klumb et al. |
| 6,251,132 | B1 | 6/2001 | Ravenscroft et al. |
| 6,254,608 | B1 | 7/2001 | Solar |
| 6,264,689 | B1 | 7/2001 | Colgan et al. |
| 6,270,521 | B1 | 8/2001 | Fischell et al. |
| 6,273,895 | B1 | 8/2001 | Pinchuk et al. |
| 6,287,322 | B1 | 9/2001 | Zhu et al. |
| 6,312,407 | B1 | 11/2001 | Zadno-Azizi et al. |
| 6,319,262 | B1 | 11/2001 | Bates et al. |
| 6,332,403 | B1 | 12/2001 | Weise et al. |
| 6,342,067 | B1 | 1/2002 | Mathis et al. |
| 6,344,053 | B1 | 2/2002 | Boneau |
| 6,348,065 | B1 | 2/2002 | Brown et al. |
| 6,358,274 | B1 | 3/2002 | Thompson |
| 6,375,676 | B1 | 4/2002 | Cox |
| 6,383,211 | B1 | 5/2002 | Staehle |
| 6,391,050 | B1 | 5/2002 | Broome |
| 6,391,051 | B2 | 5/2002 | Sullivan, III et al. |
| 6,395,020 | B1 | 5/2002 | Ley et al. |
| 6,402,760 | B1 | 6/2002 | Fedida |
| 6,413,269 | B1 | 7/2002 | Bui et al. |
| 6,443,979 | B1 | 9/2002 | Stalker et al. |
| 6,443,982 | B1 | 9/2002 | Israel et al. |
| 6,461,381 | B2 | 10/2002 | Israel et al. |
| 6,488,703 | B1 | 12/2002 | Kveen et al. |
| 6,500,248 | B1 | 12/2002 | Hayashi |
| 6,514,261 | B1 | 2/2003 | Randall et al. |
| 6,517,569 | B2 | 2/2003 | Mikus et al. |
| 6,520,983 | B1 | 2/2003 | Colgan et al. |
| 6,527,779 | B1 | 3/2003 | Rourke |
| 6,572,643 | B1 | 6/2003 | Gharibadeh |
| 6,599,296 | B1 | 7/2003 | Gillick et al. |
| 6,613,014 | B1 | 9/2003 | Chi |
| 6,613,075 | B1 | 9/2003 | Healy et al. |
| 6,629,981 | B2 | 10/2003 | Bui et al. |
| 6,645,238 | B2 | 11/2003 | Smith |
| 6,652,506 | B2 | 11/2003 | Bowe et al. |
| 6,660,031 | B2 | 12/2003 | Tran et al. |
| 6,660,827 | B2 | 12/2003 | Loomis et al. |
| 6,663,666 | B1 | 12/2003 | Quiachon et al. |
| 6,695,862 | B2 | 2/2004 | Cox et al. |
| 6,716,190 | B1 | 4/2004 | Glines et al. |
| 6,716,238 | B2 | 4/2004 | Elliott |
| 6,749,627 | B2 | 6/2004 | Thompson et al. |
| 6,755,854 | B2 | 6/2004 | Gillick et al. |
| 6,773,446 | B1 | 8/2004 | Dwyer et al. |
| 6,786,918 | B1 | 9/2004 | Krivoruchko et al. |
| 6,821,292 | B2 | 11/2004 | Pazienza et al. |
| 6,866,669 | B2 | 3/2005 | Buzzard et al. |
| 6,884,259 | B2 | 4/2005 | Tran et al. |
| 6,911,039 | B2 | 6/2005 | Shiu et al. |
| 6,913,613 | B2 | 7/2005 | Schwarz et al. |
| 6,939,352 | B2 | 9/2005 | Buzzard et al. |
| 6,939,370 | B2 | 9/2005 | Hartley et al. |
| 7,033,368 | B2 | 4/2006 | Rourke |
| 7,052,511 | B2 | 5/2006 | Weldon et al. |
| 7,122,050 | B2 | 10/2006 | Randall et al. |
| 7,172,617 | B2 | 2/2007 | Colgan et al. |
| 7,294,135 | B2 | 11/2007 | Stephens et al. |
| 7,323,006 | B2 | 1/2008 | Andreas et al. |
| 7,381,216 | B2 | 6/2008 | Buzzard et al. |
| D576,725 | S | 9/2008 | Shumer et al. |
| D578,216 | S | 10/2008 | Dorn et al. |
| D578,643 | S | 10/2008 | Shumer et al. |
| D578,644 | S | 10/2008 | Shumer et al. |
| D578,645 | S | 10/2008 | Shumer et al. |
| 7,506,650 | B2 | 3/2009 | Lowe et al. |
| 7,550,001 | B2 | 6/2009 | Dorn et al. |
| 7,553,322 | B2 | 6/2009 | Dorn et al. |
| D598,543 | S | 8/2009 | Vogel et al. |
| 7,582,054 | B2 | 9/2009 | Okada |
| 7,935,141 | B2 | 5/2011 | Randall et al. |
| 8,062,344 | B2 | 11/2011 | Dorn et al. |

(56) References Cited

U.S. PATENT DOCUMENTS

| | | |
|---|---|---|
| 8,075,606 B2 | 12/2011 | Dorn |
| 2001/0007082 A1 | 7/2001 | Dusbabek et al. |
| 2001/0044621 A1 | 11/2001 | Klumb et al. |
| 2001/0051822 A1 | 12/2001 | Stack et al. |
| 2002/0004663 A1 | 1/2002 | Gittings et al. |
| 2002/0035394 A1 | 3/2002 | Fierens et al. |
| 2002/0116044 A1 | 8/2002 | Cottone et al. |
| 2002/0151955 A1 | 10/2002 | Tran et al. |
| 2002/0183827 A1 | 12/2002 | Derus et al. |
| 2002/0188341 A1 | 12/2002 | Elliott |
| 2003/0028236 A1 | 2/2003 | Gillick et al. |
| 2003/0049295 A1 | 3/2003 | Guggenbichler et al. |
| 2003/0050686 A1 | 3/2003 | Raeder-Devens et al. |
| 2003/0074045 A1 | 4/2003 | Buzzard et al. |
| 2003/0163085 A1 | 8/2003 | Tanner et al. |
| 2003/0167060 A1 | 9/2003 | Buzzard et al. |
| 2003/0191516 A1 | 10/2003 | Weldon et al. |
| 2004/0006380 A1 | 1/2004 | Buck et al. |
| 2004/0098079 A1 | 5/2004 | Hartley et al. |
| 2004/0098083 A1 | 5/2004 | Tran et al. |
| 2004/0143160 A1 | 7/2004 | Couvillon |
| 2004/0148009 A1 | 7/2004 | Buzzard et al. |
| 2004/0153137 A1 | 8/2004 | Gaschino et al. |
| 2004/0181239 A1 | 9/2004 | Dorn et al. |
| 2004/0186547 A1 | 9/2004 | Dorn et al. |
| 2004/0193180 A1 | 9/2004 | Buzzard et al. |
| 2004/0193283 A1 | 9/2004 | Rioux et al. |
| 2004/0199240 A1 | 10/2004 | Dorn |
| 2005/0004515 A1 | 1/2005 | Hart et al. |
| 2005/0021123 A1 | 1/2005 | Dorn et al. |
| 2005/0027306 A1 | 2/2005 | Krivoruchko et al. |
| 2005/0027345 A1 | 2/2005 | Horan et al. |
| 2005/0033402 A1 | 2/2005 | Cully et al. |
| 2005/0060016 A1 | 3/2005 | Wu et al. |
| 2005/0080476 A1 | 4/2005 | Gunderson et al. |
| 2005/0085851 A1 | 4/2005 | Fiehler et al. |
| 2005/0090890 A1 | 4/2005 | Wu et al. |
| 2005/0149159 A1 | 7/2005 | Andreas et al. |
| 2005/0182475 A1 | 8/2005 | Jen et al. |
| 2005/0209670 A1 | 9/2005 | George et al. |
| 2005/0209672 A1 | 9/2005 | George et al. |
| 2005/0209674 A1 | 9/2005 | Kutscher et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2005/0288764 A1 | 12/2005 | Snow et al. |
| 2006/0058866 A1 | 3/2006 | Cully et al. |
| 2006/0074477 A1 | 4/2006 | Berthiaume et al. |
| 2006/0085057 A1 | 4/2006 | George et al. |
| 2006/0100686 A1 | 5/2006 | Bolduc et al. |
| 2006/0167467 A1 | 7/2006 | Rourke |
| 2006/0259124 A1 | 11/2006 | Matsuoka et al. |
| 2006/0276873 A1 | 12/2006 | Sato |
| 2007/0016164 A1 | 1/2007 | Dudney et al. |
| 2007/0050006 A1 | 3/2007 | Lavelle |
| 2007/0055339 A1 | 3/2007 | George et al. |
| 2007/0055342 A1 | 3/2007 | Wu et al. |
| 2007/0060999 A1 | 3/2007 | Randall et al. |
| 2007/0073379 A1 | 3/2007 | Chang |
| 2007/0073389 A1 | 3/2007 | Bolduc et al. |
| 2007/0088421 A1 | 4/2007 | Loewen |
| 2007/0100420 A1 | 5/2007 | Kavanagh et al. |
| 2007/0100422 A1 | 5/2007 | Shumer et al. |
| 2007/0100429 A1 | 5/2007 | Wu et al. |
| 2007/0112409 A1 | 5/2007 | Wu et al. |
| 2007/0118201 A1 | 5/2007 | Pappas et al. |
| 2007/0118206 A1 | 5/2007 | Colgan et al. |
| 2007/0168014 A1* | 7/2007 | Jimenez et al. ............ 623/1.12 |
| 2007/0191864 A1 | 8/2007 | Shumer |
| 2007/0191865 A1 | 8/2007 | Pappas |
| 2007/0191925 A1 | 8/2007 | Dorn |
| 2007/0194483 A1 | 8/2007 | Guggenbichler et al. |
| 2007/0233222 A1 | 10/2007 | Roeder et al. |
| 2007/0244540 A1 | 10/2007 | Pryor |
| 2007/0255390 A1 | 11/2007 | Ducke et al. |
| 2009/0024133 A1 | 1/2009 | Keady et al. |
| 2009/0099638 A1 | 4/2009 | Grewe |
| 2010/0004606 A1 | 1/2010 | Hansen et al. |
| 2010/0036472 A1 | 2/2010 | Papp |
| 2010/0094399 A1 | 4/2010 | Dorn et al. |
| 2010/0174290 A1 | 7/2010 | Wuebbeling et al. |

FOREIGN PATENT DOCUMENTS

| | | |
|---|---|---|
| DE | 03132323 A1 | 4/1983 |
| DE | 04420142 A1 | 12/1995 |
| DE | 29516712 U1 | 12/1995 |
| DE | 19539449 A1 | 4/1997 |
| DE | 29717110 U1 | 11/1997 |
| DE | 29816878 U1 | 12/1998 |
| DE | 29522101 | 12/1999 |
| DE | 19921530 | 6/2000 |
| DE | 19901530 A1 | 7/2000 |
| DE | 19936059 A1 | 2/2001 |
| DE | 20000659 U1 | 5/2001 |
| DE | 69521346 | 4/2002 |
| EP | 0436303 A1 | 7/1991 |
| EP | 0518838 A1 | 12/1992 |
| EP | 0564894 A1 | 10/1993 |
| EP | 0611556 A1 | 8/1994 |
| EP | 0630657 A1 | 12/1994 |
| EP | 0633756 B1 | 1/1995 |
| EP | 0688545 A1 | 12/1995 |
| EP | 0699451 A2 | 3/1996 |
| EP | 0712614 A1 | 5/1996 |
| EP | 0747021 A2 | 12/1996 |
| EP | 0752896 B1 | 1/1997 |
| EP | 0790041 A2 | 8/1997 |
| EP | 0792627 A2 | 9/1997 |
| EP | 0873733 A1 | 10/1998 |
| EP | 0876804 A1 | 11/1998 |
| EP | 0947212 A2 | 10/1999 |
| EP | 1025813 A2 | 8/2000 |
| EP | 1078611 A1 | 2/2001 |
| EP | 1095634 A2 | 5/2001 |
| EP | 1117341 A1 | 7/2001 |
| EP | 1132058 A1 | 9/2001 |
| EP | 1155664 A2 | 11/2001 |
| EP | 1181906 A2 | 2/2002 |
| EP | 1199051 A2 | 4/2002 |
| EP | 1290989 A2 | 3/2003 |
| EP | 1299050 B1 | 4/2003 |
| EP | 1302178 A2 | 4/2003 |
| EP | 1383446 A1 | 1/2004 |
| EP | 1440671 A2 | 7/2004 |
| EP | 1447057 A1 | 8/2004 |
| EP | 1447058 A1 | 8/2004 |
| EP | 1637092 A2 | 3/2006 |
| FR | 2760351 A1 | 9/1998 |
| FR | 2797781 A1 | 3/2001 |
| JP | 2003518406 A | 6/2003 |
| JP | 2005530558 A | 10/2005 |
| WO | WO-9521593 A1 | 8/1995 |
| WO | WO-9526775 A1 | 10/1995 |
| WO | WO-9618359 A1 | 6/1996 |
| WO | WO-9820811 A1 | 5/1998 |
| WO | WO-9823241 A2 | 6/1998 |
| WO | WO-9830173 A1 | 7/1998 |
| WO | WO-9852496 A1 | 11/1998 |
| WO | WO-9904728 A1 | 2/1999 |
| WO | WO-9925280 A1 | 5/1999 |
| WO | WO-9944541 A1 | 9/1999 |
| WO | WO-9947075 A1 | 9/1999 |
| WO | WO-9951167 A2 | 10/1999 |
| WO | WO-0000104 A1 | 1/2000 |
| WO | WO-0002503 A1 | 1/2000 |
| WO | WO-0016718 A1 | 3/2000 |
| WO | WO-0018330 A1 | 4/2000 |
| WO | WO-0071059 A1 | 11/2000 |
| WO | WO-0078246 A2 | 12/2000 |
| WO | WO-0078248 A1 | 12/2000 |
| WO | WO-0132102 | 5/2001 |
| WO | WO-0134061 A1 | 5/2001 |
| WO | WO-0147436 A2 | 7/2001 |

(56) References Cited

FOREIGN PATENT DOCUMENTS

| WO | WO-0158387 | A1 | 8/2001 |
|----|------------|----|----|
| WO | WO-0189421 | | 11/2001 |
| WO | WO-0203888 | A2 | 1/2002 |
| WO | WO-0203889 | A2 | 1/2002 |
| WO | WO-02066094 | A2 | 8/2002 |
| WO | WO-02083036 | A2 | 10/2002 |
| WO | 02087470 | A1 | 11/2002 |
| WO | WO 02087470 | A1 * | 11/2002 |
| WO | WO-02102279 | A2 | 12/2002 |
| WO | WO-03002020 | A2 | 1/2003 |
| WO | 03061724 | A2 | 7/2003 |
| WO | WO-2005004515 | A1 | 1/2005 |
| WO | WO-2005039448 | A1 | 5/2005 |
| WO | WO-2005053574 | A2 | 6/2005 |
| WO | 2005062980 | A2 | 7/2005 |
| WO | 2005065200 | A2 | 7/2005 |
| WO | 2005117759 | A2 | 12/2005 |
| WO | WO-2006104143 | A1 | 10/2006 |
| WO | 2007002713 | A2 | 1/2007 |
| WO | 2007005799 | A1 | 1/2007 |
| WO | 2007022395 | A1 | 2/2007 |
| WO | 2007029242 | A1 | 3/2007 |
| WO | WO-2007044929 | A1 | 4/2007 |
| WO | WO-2007083470 | A1 | 7/2007 |
| WO | WO-2008034793 | A1 | 3/2008 |

OTHER PUBLICATIONS

EP 10001359.8 filed Aug. 16, 2006 European Search Report dated May 28, 2010.
U.S. Appl. No. 10/476,351, filed May 7, 2004 Notice of Allowance dated Mar. 12, 2009.
U.S. Appl. No. 11/144,513, filed Jun. 3, 2005 Advisory Action dated Oct. 5, 2010.
U.S. Appl. No. 11/144,513, filed Jun. 3, 2005 Final Office Action dated Jul. 13, 2010.
U.S. Appl. No. 11/144,513, filed Jun. 3, 2005 Final Office Action dated Oct. 15, 2008.
U.S. Appl. No. 11/144,513, filed Jun. 3, 2005 Final Office Action dated Oct. 20, 2009.
U.S. Appl. No. 11/144,513, filed Jun. 3, 2005 Non-Final Office Action dated Feb. 2, 2010.
U.S. Appl. No. 11/144,513, filed Jun. 3, 2005 Non-Final Office Action dated Feb. 5, 2008.
U.S. Appl. No. 11/144,513, filed Jun. 3, 2005 Non-Final Office Action dated Feb. 26, 2009.
U.S. Appl. No. 11/505,185, filed Aug. 16, 2006 Non-Final Office Action dated Mar. 31, 2010.
U.S. Appl. No. 11/505,185, filed Aug. 16, 2006 Non-Final Office Action dated Oct. 7, 2010.
U.S. Appl. No. 11/652,737, filed Jan. 12, 2007 Advisory Action dated Aug. 27, 2010.
U.S. Appl. No. 11/652,737, filed Jan. 12, 2007 Final Office Action dated Jun. 10, 2010.
Nov. 30, 2007 International Search Report in international application No. PCT/EP2007/058205 filed on Aug. 7, 2007.
Nov. 30, 2007 Written Opinion of the International Searching Authority in international application No. PCT/EP2007/058205 filed on Aug. 7, 2007.
Aug. 4, 2008 International Preliminary Report on Patentability in international application No. PCT/EP2007/058205 filed on Aug. 7, 2007.
Nov. 4, 2008 International Search Report in international application No. PCT/EP2008/059040 filed on Jul. 10, 2008.
Nov. 4, 2008 Written Opinion of the ISA in international application No. PCT/EP2008/059040 filed on Jul. 10, 2008.
Sep. 29, 2009 International Preliminary Report on Patentability in international application No. PCT/EP2008/059040 filed on Jul. 10, 2008.
Jul. 17, 2009 Non-final Office Action in U.S. Appl. No. 10/824,033, filed Apr. 14, 2004.
Dec. 15, 2005 International Search Report in international application No. PCT/US2005/019860 filed on Jun. 6, 2005.
Dec. 15, 2005 Written Opinion of the international searching authority in international application No. PCT/US2005/019860 filed on Jun. 6, 2005.
Dec. 4, 2006 International Preliminary Report on Patentability in international application No. PCT/US2005/019860 filed on Jun. 6, 2005.
Apr. 27, 2007 Written Opinion of the ISA in international application No. PCTUS2007000834 filed on Jan. 12, 2007.
Jul. 15, 2008 International Preliminary Report on Patentability in international application No. PCTUS2007000834 filed on Jan. 12, 2007.
Jan. 19, 2007 International Search Report in international application No. PCT/US2006/032228 filed on Aug. 16, 2006.
Jan. 19, 2007 Written Opinion of the ISA in international application No. PCT/US2006/032228 filed on Aug. 16, 2006.
Feb. 20, 2008 International Preliminary Report on Patentability in international application No. PCT/US2006/032228 filed on Aug. 16, 2006.
Apr. 27, 2007 International Search Report in international application No. PCT/US2007/000834 filed on Jan. 12, 2007.
"Medtronic Announces FDA Clearance of Bridge SE Biliary Stent." Business Wire, Oct. 15, 2001. www.medtronic.com/newsroom/news_20011015a.html.
"Summary for the Bridge SE Biliary Self-Expanding Stent Delivery System" Jan. 14, 2002 FDA Section 510 (k) review.
Jul. 10, 2002 International Search Report in international application No. PCT/EP2002/04727 filed on Apr. 29, 2002.
Jan. 7, 2003 International Preliminary Examination Report in international application No. PCT/EP2002/04727 filed on Apr. 29, 2002.
Aug. 31, 2009 Non-Final Office Action in U.S. Appl. No. 11/505,185, filed Aug. 16, 2006.
Nov. 12, 2008 Non-Final Office Action in U.S. Appl. No. 11/652,737, filed Jan. 12, 2007.
May 27, 2009 Final Office Action in U.S. Appl. No. 11/652,737, filed Jan. 12, 2007.
Oct. 27, 2009 Non-Final Office Action in U.S. Appl. No. 11/652,737, filed Jan. 12, 2007.
Apr. 4, 2008 Non-Final Office Action in U.S. Appl. No. 10/476,351, filed May 7, 2004.
Oct. 21, 2008 Final Office Action in U.S. Appl. No. 10/476,351, filed May 7, 2004.
Feb. 4, 2009 Final Office Action in U.S. Appl. No. 10/476,351, filed May 7, 2004.
Jan. 21, 2004 International Search Report in international application No. PCT/EP2002/06784 filed on Jun. 19, 2002.
Apr. 14, 2004 International Preliminary Examination Report in international application No. PCT/EP2002/06784 filed on Jun. 19, 2002.
JP 2008-550429 filed Jun. 27, 2008 Office Action dated Jan. 4, 2012.
U.S. Appl. No. 12/640,956, filed Dec. 17, 2009 Non-Final Office Action dated Jan. 24, 2011.
U.S. Appl. No. 12/640,956, filed Dec. 17, 2009 Notice of Allowancwe dated Jul. 13, 2011.

* cited by examiner

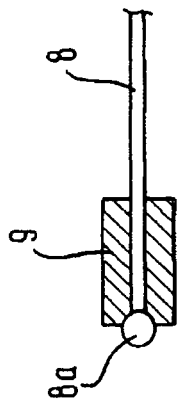
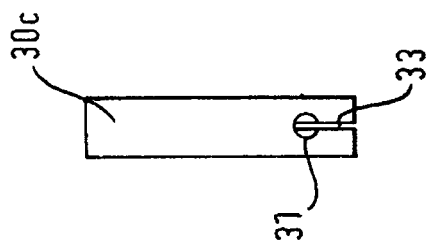
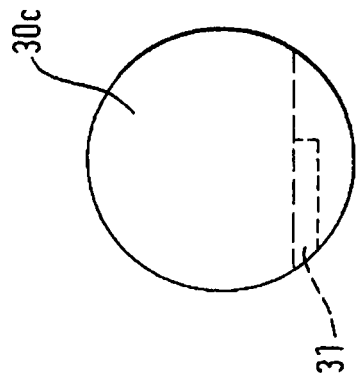
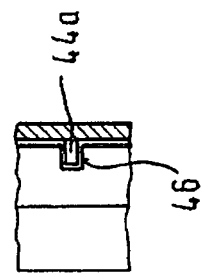

HAND-HELD ACTUATOR DEVICE

PRIORITY

This application is a U.S. national stage application under 35 USC §371 of International Application No. PCT/EP2007/058205, filed Aug. 7, 2007, claiming priority to Great Britain Patent Application No. 0615658.2, filed Aug. 7, 2006, each of which is incorporated by reference in its entirety into this application.

BACKGROUND OF THE INVENTION

1. Field of the Invention

The present invention relates generally to a catheter based system for treating a remote location within a patient and more particularly to the hand-held actuator devices of stent delivery systems.

2. Background

A delivery system for a self-expanding stent usually has the stent distally adjacent to a tube, both within a sleeve at the distal end of a catheter. To deliver the stent, the sleeve has to be pulled back while the tube holds the stent from moving back with the sleeve. Therefore, the tube is placed adjacent to the stent and acts as a barrier and restrains the stent from moving while the sleeve is pulled back.

WO 02/087470 discloses a hand device for a catheter stent delivering system. The hand device can be operated one-handed to ease the operation with such a device. The main function such devices have to include are:
1) to pull back the sleeve, for example by pulling a wire which is connected to the proximal end of the outer sleeve;
2) to restrain simultaneously the inner tube from being pulled back together with the sleeve; and
3) to provide a visual signal of how much length of the sleeve has already been pulled back The restraint function can be performed by a hub that is mounted within the hand-held actuator and itself receives the proximal end of the tube. To pull the wire, in WO 02/087470 is provided an index-finger-triggering-system, which causes a mechanical apparatus within the device to pull in the wire and draw the proximal end of the sleeve into the housing of the hand unit. A disadvantage of the index-finger-triggering-system is that it is a pistol-like device and the impression it gives to the operator, of direct tactile feedback about the progress of stent release, some operators might find unconvincing. Furthermore, the maximum length of wire, which can be reeled in by successive squeezes of the trigger, is defined by the length of the, track in the hand unit along which the proximal end of the sleeve advances proximally, rendering it incapable of releasing a self-expanding stent which is longer than the track.

EP 1 299 050 discloses a thumb-actuating-screwing-system, but this has all disadvantages of the index-finger-triggering-system. In addition the thumb has to be lifted between every turn of the screw, which makes the control of the pull-mechanism less comfortable.

Both of the above identified systems have a component protruding from the housing of the hand unit, which moves proximally through the device with the catheter being withdrawn, and so acts as a distance indicator. When the operator starts coiling-up the wire, the indicator moves and the operator and his or her assistants can judge the extent of the progressive stent release from the distance the indicator has travelled proximally along the length of the housing of the hand unit.

Stents are getting longer (e.g. in a leg the stent can be about 30 cm). It is one object of the present invention to provide a hand-held actuator for release of a self-expanding stent with a length longer than can be handled by the known hand-held actuators.

Generally, the present invention aims to improve on the performance of the devices of WO 02/087470 and EP 1 299 050, in the respects mentioned above.

SUMMARY OF THE INVENTION

According to the present invention there is provided a device for releasing into the body from a delivery system a medical prosthesis, like a stent, of the form discussed above and defined in claim 1, claim 16 or claim 18. According to the present invention there is provided a stent delivery system as defined in claim 20. Optional or preferred features of the invention are mentioned in the dependent claims.

In a first preferred embodiment, the device comprises a frame, which can be moulded of plastic and acts as housing. At its distal end a hub is provided, which acts as an abutment system for the tube. A slider is connected in a one-way connection to a reel, which is caused to rotate by a pull stroke of the slider. The reel winds a portion of a length of the wire by every pull stroke and holds the position by every return stroke. A detent restrains the reel from moving during a return stroke, so the reel is urged to move in only one direction.

In a second embodiment the slider is formed as a thumb pad and has a carriage portion on his flanks. It slides on a track, which is defined by the frame. In a rest position, the slider is restrained from sliding by a slider release element, which is located within the thumb pad and which prevents the wire inadvertently being pulled proximally. In the restraining initial position the slider release element protrudes from the carriage portion of the slider. The slider release element can be urged in a second release position, which allows the slider to move free on the track.

Particularly when the slider slides on a track in a direction parallel to the axis of the catheter, the operator has the sensation that the thumb pad delivers useful tactile feedback about what happening at the distal end of the catheter, where the stent is being released.

In a third embodiment, the one-way connection comprises teeth on a elongation of the slider element and co-operating teeth on a rotatory element which is operatively connected to the reel. The one-way connection could be located between the teeth of the slider and the rotatory element. In this case the teeth are formed such that they engage in one way and slip over in the reverse direction. Such embodiment can enhance the sensation of tactile feedback to the operator, through the wire and reel to the slider.

In another embodiment the detent is formed as a pawl to engage with the reel or, more specifically, with the teeth of the rotatory element, to restrain it from moving in the reverse direction. This finger preferably points in the rotatory direction of the wheel. In another construction of the detent a finger engages with the wire such that the finger pushes the wire onto the reel. In this case the restraining force comes from the resilience of the wire in addition to the friction between the wire and the finger. In a further embodiment, the detent comprises both the pawl and the finger. Embodiments that include such a pawl can provide audible feedback to the operator (and others working with the operator), in the form of clicking sounds, about the rate of progress of the stent release operation.

These embodiments can be used with stent delivery catheters, both 'over the wire' and 'rapid exchange'. They can be used regardless whether it is the inner or the outer element of the co-axial shaft of the catheter which is proximally withdrawn relative to the other to release the stent. A catheter system which employs the inner of two co-axial shaft elements to pull proximally back a sheath that surrounds a self-expanding stent at the distal end of the catheter is called a 'pull-wire' stent delivery catheter. Such a pull wire system is useful for delivering ultra-long stents, because the reel can accommodate a length of the pull wire longer than the stent, however long the stent is.

The described embodiments need very few mechanical elements. This avoids unnecessary waste and minimizes assembly time and weight of the device. Furthermore, with the pull wire of the catheter system connected directly to the reel there is no limit to the length of wire that can be withdrawn proximally. With relatively short stents, when placement in the body is delicate, the slider can still act as an indicator of stent release progress, and how much of the stent length is still to be released.

The design of the device can be formed ergonomically such it is comfortable for every hand size of any operator. In addition, the thumb of the gripping hand falls naturally on the thumb pad of the slider.

Recapitulating some advantages of the present invention over the above mentioned prior art systems are:
 better tactile feedback about the stent delivery progress
 no limitation of the stent length, with simultaneous visual information about the stent delivery progress
 stepless wire-pulling and audible feedback of the operation progress
 improved handling through ergonomic design
 reduced number of mechanical components

BRIEF DESCRIPTION OF THE FIGURES

FIG. 4 is a side view to show a borehole and a groove in the cylindrical drum of the reel;
FIG. 5 is a front view of the drum of FIG. 4;
FIG. 6 is a side view of an end of the wire;
and
FIG. 7 is a section along the line IV-IV in FIG. 3 seen from above.

DETAILED DESCRIPTION

The invention can be embodied in a device for pulling a wire 8 out of a tube 14 and which can be activated, preferably with only one hand.

Figure 1:
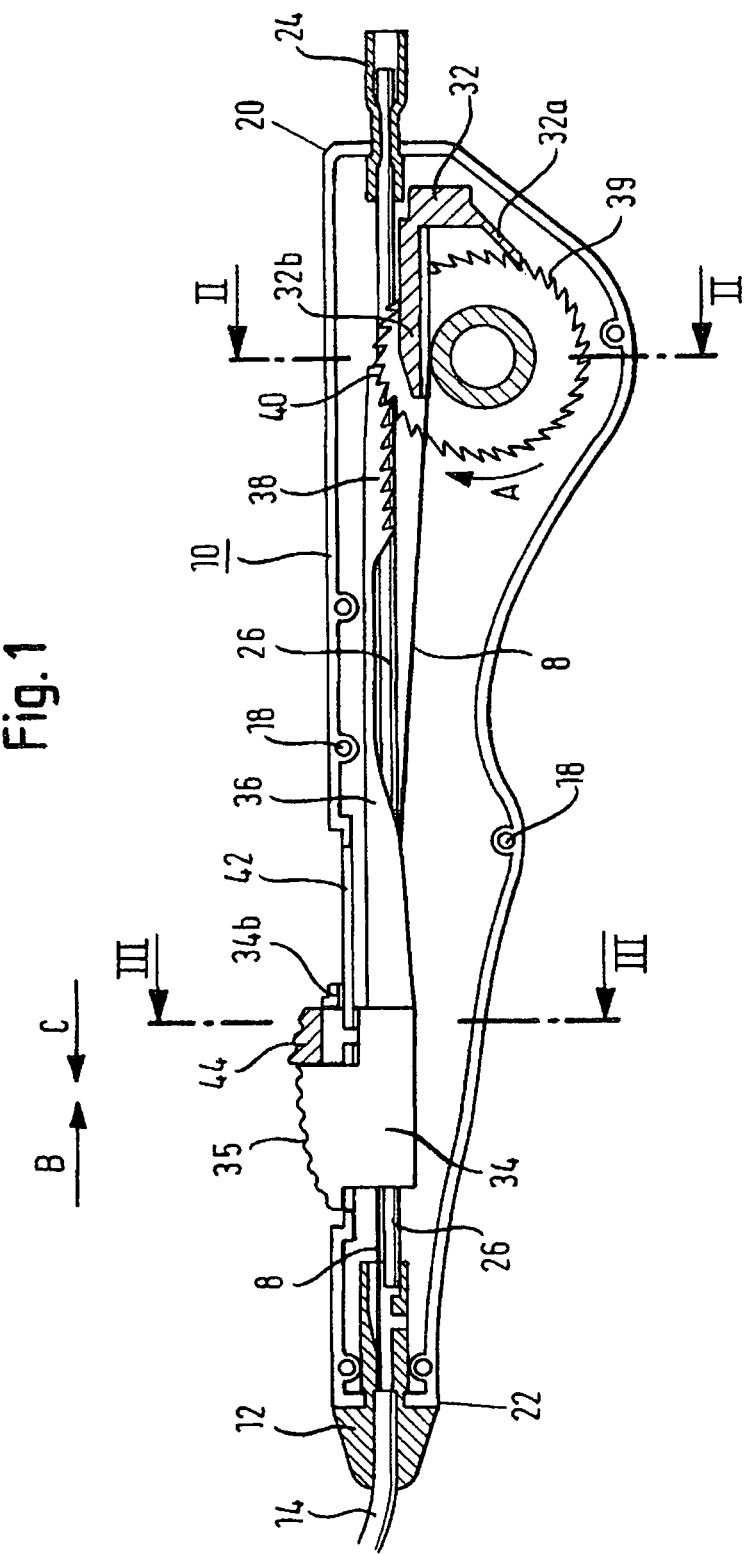
FIG. 1 shows a longitudinal section of a preferred embodiment.

The drawings show a preferred embodiment of the invention. FIG. 1 shows one half of a moulded housing 10 which serves as a frame for mounting the various components of the device, and has a proximal end 20 and a distal end 22. The housing is almost symmetric and the two half housing parts are fixed together with screws 18 (or something similar like rivets or plugs) at defined places. A portion of each half of the housing is covered with a rubber material (not shown). This increases the grip and eases the handling of the device.

A first hub 12 is fixed at the distal end 22 of the housing, acting as an abutment and bearing element for guiding the tube 14 to the housing 10. The tube 14 terminates in the hub 12, so that a wire 8 can be pulled out of the tube. The hub 12 acts as an abutment element and stops the tube 14 from being pulled into the housing 10. Through this abutment element extends an inner tube 26 to a second hub 24 at the proximal end 20 of the housing 10. The second hub 24 provides a female luer connector to engage a corresponding male luer, for flushing liquid for the lumen of the tube 14.

Figure 3:
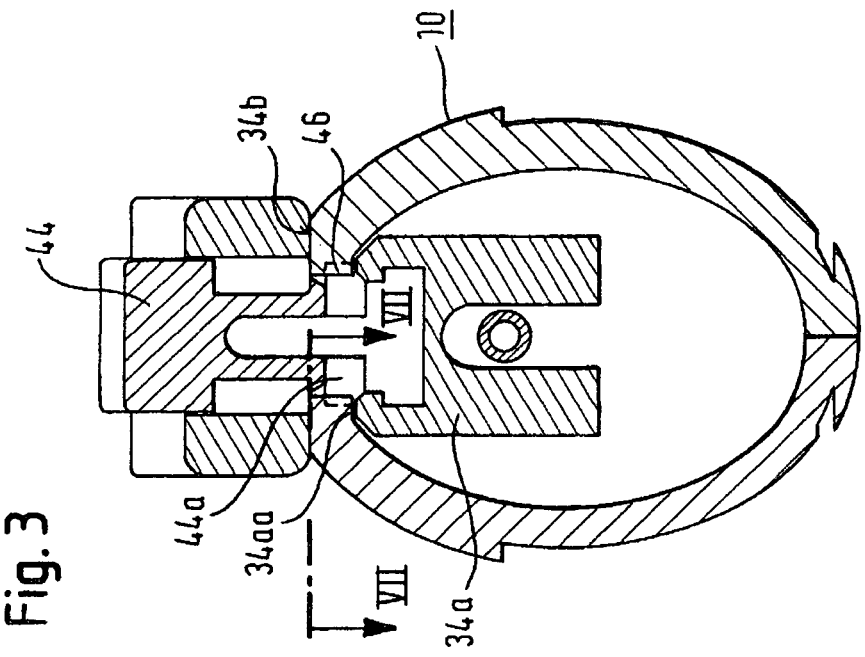
FIG. 3 shows a transverse section along the line in FIG. 1.

A reel 30 is provided to take up the wire 8 and is preferably near the proximal end 20 of the housing 10 rotatably mounted in the housing. The reel is flanked by two large discs 30a, 30b, spaced apart by a cylindrical drum surface 30c of the reel for the wire. Both of the discs have a toothed circumferential surface to provide a ratchet element (see FIG. 3). In other embodiments there could be only one smooth wheel and one ratchet wheel instead of both wheels being ratchet wheels.

The reel coils up the wire when it rotates in the direction of arrow A and would release the wire if it were able to rotate in the opposite direction.

To attach the wire 8 to the reel 30 there is provided a special ball-end on the wire and 8 a borehole in the drum 30c.

With reference to FIGS. 4, 5 and 6 a borehole 31 is provided in the cylindrical drum 30c. The borehole 31 leads from the surface of the cylindrical drum 30c, in a direction transverse to the rotatory axis into the drum 30c, to an abutment surface 31c. A groove 33 co-axial with the borehole 31 links the borehole with the surface of the drum.

The end of the wire 8 carries a sleeve 9 and a ball 8a, welded to the end of the wire 8. The wire 8 is put with the free end into the sleeve 9 and the ball 8a stops the wire 8 from sliding through the sleeve 9. Another way fixing the sleeve 9 to the wire 8 could be to weld the ball 8a on the wire 8 after putting it through the sleeve 9.

In another embodiment the wire and the sleeve are pressed together such the sleeve 9 is fixed on the wire.

The wire 8 is threaded into the groove 33 and the sleeve 9 is advanced into the borehole 31. Pulling the wire urges the sleeve to slide into the first borehole 31a, which has a diameter slightly bigger than the sleeve 9, and blocks the wire from being pulled further.

To avoid releasing a coiled up wire, a backstroke-stopper 32 (otherwise called 'detent') is provided near the reel 30. In the preferred embodiment the stopper has two fingers. The first is a detent 32a which functions as a pawl by engaging the teeth of the ratchets 30a and/or 30b. The teeth of the ratchets are so shaped that the finger 32a does not prevent the ratchet from rotating in direction A, but stops the reel rotating in the other direction by engaging into a gap between adjacent teeth.

Figure 2:
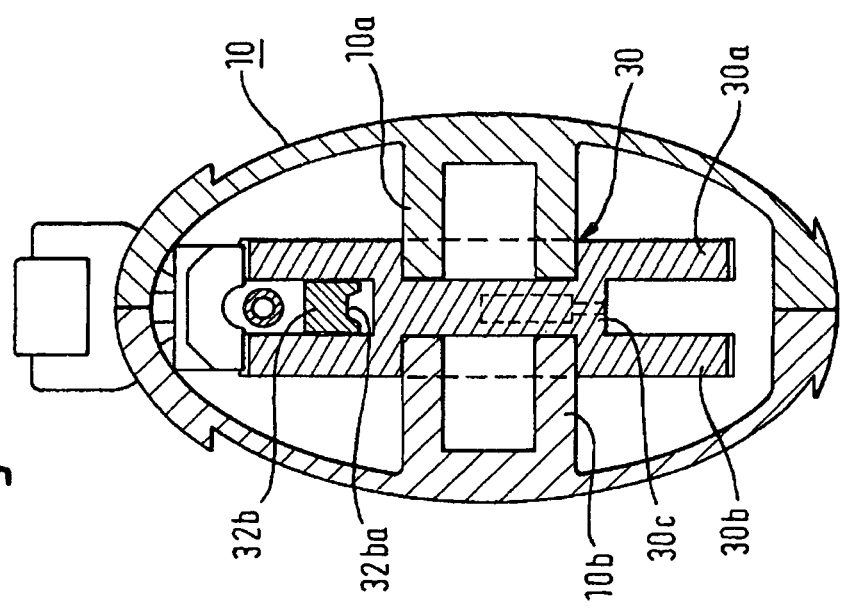
FIG. 2 shows a transverse section along the line II-II in FIG. 1.

The second finger 32b serves to press the already coiled wire towards the rotational axis of the reel. The wire is springy so it tends to straighten when it can and so will tend to unroll from the reel. The second finger prevents this happening. Preferably the second finger 32b has a recess 32ba (as shown in FIG. 2) facing the wire to receive the wire 8. When the second finger 32b presses down the wire 8, there is friction between the wire and the finger. This friction, together with the resilience of the wire, can act as a brake in the rotation of the reel. Indeed, such a brake can render any ratchet and pawl superfluous. One advantage of a brake over a ratchet in that one can achieve a stepless pulling of the wire 8.

To urge the reel to rotate to wind in the wire 8, in direction A, a slider 34 is provided. This slider has a thumb pad 35 and is operably connected to the reel by its elongate extension 36 that has a toothed straight ratchet profile 38 at its end remote from the thumb pad. The toothed straight profile 38 and the toothed ratchet on the periphery of each of the reel discs 30a, 30b provide a one-way-connection 40 in which the reel rotates when the slider is moved in the direction of arrow B. When the discs are so urged to rotate, the drum 30c between the two discs is also rotating and the wire is coiled up. When the slider is urged in the reverse direction, arrow C, the teeth of the straight ratchet slide over the teeth of the discs (see 40). In another embodiment the straight ratchet and the discs may ba fixedly connected such that both move together, in both directions. A one-way bearing in the hub of the reel allows the wire take-up reel to rotate in the direction of arrow A, but not in direction of arrow B. Of course the movement directions of the particular elements are changeable at will. For example, if the wire coils up anti-clockwise on the reel, rather than clockwise, each would be arranged the other way.

The slider slides on a track 42, defined by the housing 10. The slider includes a slider release element 44, that is moveable between a relaxed gripping disposition and a pushed down release disposition. The release element, when not pushed down, is formed such that a detent 44*a* of the slider release element is blocked by a recess 46 the housing (as shown in FIG. 7). This restrains inadvertent sliding of the slider. When the slider is to be moved, the slider release element is first pushed down until the detent engages the corresponding locker element 34*aa* on the inner part of the slider 34*a* and is being held down. As a result the slider 34 is released from the recess 46 in the housing and is free to move along the track 42.

In another embodiment there could be provided a distance scale (not shown) next to the sliding track advancing the distance indication by the slider.

In another embodiment, there is provided a spring (not shown) in the housing 10, which is connected to the slider and urges the slider to slide back into the first pull back position automatically.

As soon as the slider release element 44 is no longer pushed down, it moves up again as a result of its resilience and the ramps 44*a* and 34*aa*, once again to restrain slider movement.

In the present embodiment all device members (reel, housing, slider, head, hub and stopper) are moulded from plastics. In other embodiments components can be provided as separate individual parts (e.g. the reel in one smooth, smaller wheel and two ratchets). These parts can be formed of various materials (e.g. metal, different kinds of plastics) and assembled (by screwing, plugging, welding, riveting) as desired.

The invention claimed is:

1. A device for pulling a length of wire out of a tube having front and back ends comprising:
    a reel for receiving the length of wire;
    a frame to which the reel is mounted, the frame including an abutment for the back end of the tube;
    a manually operable slider mounted to the frame for a stroke of backward movement and a stroke of forward movement;
    a connection
        that engages the slider and the reel when the slider moves backward, configured to rotate the reel about an axis to wind a portion of the length of wire onto the reel
        and
        that disengages the slider and the reel when the slider moves forward and returns to the start of the backward stroke;
    and
    a detent that restrains the reel from rotation during the forward stroke.

2. The device according to claim 1 wherein the slider has a carriage portion that slides on a track defined by the frame.

3. The device according to claim 2 including a slider release element that, in an initial disposition, restrains the slider from moving on the track and, in a release disposition, allows the slider to move on the track.

4. The device according to claim 3 wherein the slider release element is located within a thumb pad that protrudes from the carriage portion of the slider.

5. The device according to claim 1 wherein the slider slides next to a distance scale to indicate how much the slider has moved.

6. The device according to claim 1 wherein the connection comprises teeth on the slider and co-operating teeth on an element connected to the reel.

7. The device according to claim 6 wherein the connection comprises the teeth on the slider and the teeth on the element, wherein the teeth engage during the backward stroke and slip over each other during the forward stroke.

8. The device according to claim 1 wherein the detent comprises at least one resilient finger.

9. The device according to claim 1 wherein the detent is formed such that it pushes down the wire on the reel.

10. The device according to claim 9 wherein the force to restrain the reel from rotation during the forward stroke comes from the resilience of the wire in addition to the friction between the wire and the detent.

11. The device according to claim 1 wherein the detent comprises a pawl that engages teeth to restrain movement of the reel.

12. The device according to claim 1 further including means for attaching one end of the wire to the reel.

13. The device according to claim 1 further including a first hub mounted at the front end of the frame and a second hub mounted at the back end of the frame being connected by an inner tube.

14. The device according to claim 1 composing a pull wire system for deploying a trans-luminal, catheter-mounted, self-expanding stent.

15. A device for pulling a length of wire out of a tube having front and back ends comprising:
    a reel for receiving the length of wire and means for fixing one end of the wire to the reel;
    a frame to which the reel is mounted, the frame including an abutment for the back end of the tube;
    a manually operable slider mounted to the frame for a stroke of backward movement and a stroke of forward movement;
    a connection
        that engages the slider and the reel when the slider moves backwards, configured to rotate the reel about an axis to wind a portion of the length of wire onto the reel and
        and
        that disengages the slider and the reel when the slider moves forward and returns to the start of the backward stroke;
    wherein the connection comprises teeth on the slider and co-operating teeth on an element connected to the reel, wherein the teeth on the slider and the teeth on the element engage with each other during the backward stroke and slip over each other during the forward stroke;
    a detent that restrains the reel from rotation during the forward stroke.

16. The device according to claim 15 further including a first hub mounted at the front end of the frame and a second hub mounted at the back end of the frame and being connected by an inner tube.

17. A device for pulling a length of wire out of a tube having front and back ends comprising:
    a reel for receiving the length of wire and means for fixing one end of the wire to the reel;

a frame to which the reel is mounted, the frame including an abutment for the back end of the tube;
a first hub mounted at the front end of the frame to receive the back end of the tube;
a manually operable slider mounted to the frame for a stroke of backward movement and a stroke of forward movement;
a connection
that engages the slider and the reel when the slider moves backwards, configured to rotate the reel about an axis that winds a portion of the length of wire onto the reel
and
that disengages the slider and the reel when the slider moves forward and returns to the start of the backward stroke;
and
a detent that restrains the reel from rotation during the forward stroke.

18. The device according to claim 17 further including a second hub mounted at the back end of the frame and connected by an inner tube to the first hub whereby the tube can be flushed by liquid via the second hub and the inner tube.

19. A pull wire system for deploying a trans-luminal, catheter mounted, self-expanding stent by pulling a length of wire out of a tube having front and back ends comprising:
a reel for receiving the length of wire and means for fixing one end of the wire to the reel;
a frame to which the reel is mounted, the frame including an abutment for the back end of the tube;
a manually operable slider mounted to the frame for a stroke of backward movement and a stroke of forward movement;
a first hub mounted at the front end of the frame to receive the back end of the tube;
a connection
that engages the slider and the reel when the slider moves backward to rotate the reel about an axis to wind a portion of the length of wire onto the reel
and
that disengages the slider and the reel when the slider moves forward and returns to the start of the backward stroke;
wherein the connection comprises teeth on the slider and co-operating teeth on a an element connected to the reel, wherein the teeth on the slider and the teeth on the element engage with each other during the backward stroke and slip over each other during the forward stroke; and
a detent that restrains the reel from rotation during the forward stroke.

20. The pull wire system according to claim 19 further including a first hub mounted at the front end of the frame and a second hub mounted at the back end of the frame and connected by an inner tube.

* * * * *